United States Patent
Zhang et al.

(10) Patent No.: US 10,722,688 B2
(45) Date of Patent: Jul. 28, 2020

(54) DEVICE AND LIQUID COMPOSITIONS FOR SECURING CATHETERS HAVING A RIGID TAPERED TIP

(71) Applicant: ADHEZION BIOMEDICAL, LLC, Wyomissing, PA (US)

(72) Inventors: Sheng Zhang, Hickory, NC (US); Amanda Guido, Granite Falls, NC (US); Rafael Ruiz, Sr., Hudson, NC (US)

(73) Assignee: Adhezion Biomedical, LLC, Wyomissing, PA (US)

( * ) Notice: Subject to any disclaimer, the term of this patent is extended or adjusted under 35 U.S.C. 154(b) by 30 days.

(21) Appl. No.: 15/812,541

(22) Filed: Nov. 14, 2017

(65) Prior Publication Data

US 2019/0143081 A1 May 16, 2019

(51) Int. Cl.
*A61M 25/02* (2006.01)
*A61L 24/06* (2006.01)
*C09J 4/00* (2006.01)
*A61B 17/00* (2006.01)

(52) U.S. Cl.
CPC ....... *A61M 25/02* (2013.01); *A61B 17/00491* (2013.01); *A61L 24/06* (2013.01); *C09J 4/00* (2013.01); *A61B 2017/00004* (2013.01); *A61M 2025/0266* (2013.01)

(58) Field of Classification Search
CPC .......... A61M 25/02; A61M 2025/0266; A61M 35/003; A61B 17/00491; A61L 24/06; C09J 4/00; B65D 35/36; B65D 51/225
USPC .................................................. 401/132–135
See application file for complete search history.

(56) References Cited

U.S. PATENT DOCUMENTS

| | | | |
|---|---|---|---|
| 849,110 A * | 4/1907 | Erickson | B43K 5/14 220/277 |
| 4,413,753 A | 11/1983 | Stock | |
| 4,507,111 A * | 3/1985 | Gordon | A47K 7/028 401/134 |
| 4,685,591 A | 8/1987 | Schaefer et al. | |
| 5,649,648 A | 7/1997 | Lier et al. | |
| 5,928,611 A | 7/1999 | Leung | |
| 6,099,807 A | 8/2000 | Leung | |
| 6,322,852 B1 | 11/2001 | Leung | |
| 6,340,097 B1 | 1/2002 | D'Alessio et al. | |
| 6,376,019 B1 | 4/2002 | Leung | |
| 6,494,896 B1 | 12/2002 | D'Alessio et al. | |
| 6,547,467 B2 * | 4/2003 | Quintero | A61B 17/00491 206/438 |
| 6,676,322 B1 | 1/2004 | Leung | |
| 6,705,790 B2 | 3/2004 | Quintero et al. | |
| 6,779,657 B2 | 8/2004 | Mainwaring et al. | |
| 6,960,040 B2 | 11/2005 | D'Alessio et al. | |

(Continued)

OTHER PUBLICATIONS

Adhezion: "SecurePortIV(TM) Demo Setup"; Oct. 24, 2017 (Oct. 24, 2017); p. 1; XP054979126; Retrieved from the Internet: URL:https://www.youtube.com/watch?v=WBNgGZ SxjEE [retrieved on Feb. 12, 2019] the whole document.

(Continued)

*Primary Examiner* — Nicholas J. Weiss
(74) *Attorney, Agent, or Firm* — Stradley Ronon Stevens and Young, LLP

(57) ABSTRACT

An applicator for storing, sterilizing, and dispensing adhesives. The applicator includes a rigid tapered tip, a body, and a container holding a polymerizable cyanoacrylate monomer adhesive. The applicator is sterilized by radiation and, following sterilization, the adhesive remains substantially unpolymerized for about twenty-four months.

19 Claims, 2 Drawing Sheets

(56) References Cited

U.S. PATENT DOCUMENTS

| | | | |
|---|---|---|---|
| 7,128,241 B2 | 10/2006 | Leung | |
| 7,297,217 B2 | 11/2007 | DeWitt | |
| 7,306,390 B2 | 12/2007 | Quintero et al. | |
| 7,516,872 B2 * | 4/2009 | Boone | A61B 17/00491 |
| | | | 206/532 |
| 2002/0176732 A1 | 11/2002 | Quintero et al. | |
| 2006/0282035 A1 | 12/2006 | Battisti et al. | |
| 2007/0147947 A1 | 6/2007 | Stenton et al. | |
| 2008/0105580 A1 | 5/2008 | Nentwick et al. | |
| 2008/0167681 A1 | 10/2008 | Stenton | |
| 2013/0004230 A1 * | 1/2013 | Kirk, III | A45D 34/04 |
| | | | 401/132 |
| 2013/0108352 A1 | 5/2013 | Ruiz, Sr. et al. | |

OTHER PUBLICATIONS

International Search Report for International Application No. PCT/US2018/060636 issued by the European Patent Office dated Feb. 21, 2019.

U.S. Food and Drug Administration: "501(k) Premarket Notification K170505 for SecurePortIV Catheter Securement Adhesive;" Oct. 31, 2017; XP055554882; Retrieved from the Internet: URL:https//www.accessdata.fda.gov/cdrh_do cs/pdf17/K170505.pdf.

Budgen et al., "Skin Glue Reduces the Failure Rate of Emergency Department—Inserted Peripheral Intravenous Catheters: A Randomized Controlled Trial", Annals of Emergency Medicine, 68(2), 196-201, (2016).

Klein et al., "2-Octyl Cyanoacrylate Glue for the Fixation of Continuous Peripheral Nerve Catheters", Anesthesiology, 98(2), 590-591, (2003).

Simonova et al., "Cyanoacrylate tissue adhesives—effective securement technique for intravascular catheters: in vitro testing of safety and feasibility", Anaesthesia and Intensive Care, 40, 460-466, (2012).

Wilkinson et al., "Securing epidural catheters with Histoacryl glue", Anaesthesia, 63, 324, (2008).

Wilkinson et al., "Tissue adhesive as an alternative to sutures for securing central venous catheters", Anaesthesia, 62, 969-970, (2007).

* cited by examiner

DEVICE AND LIQUID COMPOSITIONS FOR SECURING CATHETERS HAVING A RIGID TAPERED TIP

TECHNICAL FIELD

This invention relates generally to the field of applicator devices for storing and applying adhesives. More particularly, the invention relates to a serializable applicator with a rigid tapered tip used to secure catheters.

BACKGROUND OF THE INVENTION

Reliable venous access is critical for the safe and effective care of millions of patients every year around the world. In the United States alone roughly 330 million intravascular devices are purchased by hospitals each year, and 60% to 90% of hospitalized patients require an IV catheter during their hospital stay.

Current peripheral catheter securement dressings can be divided into three broad categories: tape/transparent dressings, plastic shields, and adhesive anchors. Recent scientific literature demonstrates that even with the strictest adherence to these current standards, early failure rates are as high as 35-50% when current catheter securement dressing products are utilized. Failure prior to the end of therapy leads to increased trauma and risk of complications as the patient undergoes re-insertion to gain venous access to continue their treatment protocol. The most common complications include dislodgement, phlebitis, and catheter-related bloodstream infections (CRBSI). Reducing the frequency of complications associated with catheter movement can, in turn, reduce the occurrence of needle stick injuries for health care workers and prevent otherwise unnecessary costs for hospital stays.

As a result of the complications associated with IV catheter use, the development of reliable yet cost-effective securement techniques is extremely important. Preliminary studies indicated that a cyanoacrylate adhesive may address this significant problem. In a recent study by Bugden and colleagues peripheral intravenous catheter failure was 10% lower (95% confidence interval—18% to 2%; P=0.02) with skin glue (17%) than standard care (27%), and dislodgement was 7% lower (95% confidence interval—13% to 0%; P=0.04). Wilkinson and Fitz-Henry used a butyl cyanoacrylate to affix epidural catheters and reduced the fall-out rate from 12.3% to 3.8%. The fixation method by cyanoacrylate adhesive was found to be "highly acceptable to the patients" and simple to perform. Klein et al described the use of cyanoacrylate to secure continuous peripheral nerve catheters and, based on their findings, suggested that it could be used in highly mobile locations and even "areas subject to perspiration." Because of the toughness, durability, and high mechanical strength that a cyanoacrylate adhesive bond provides, Wilkinson, Sheikh, and Jayamaha chose cyanoacrylate for securing central venous catheters, a procedure commonly carried out using sutures; the cyanoacrylate technique reduced patient pain and discomfort from both suturing and removal while also providing a cost benefit. Simonova et al evaluated the use of cyanoacrylate for catheter securement in vitro and found that the adhesives "significantly increased the pull-out force" while being "quick and easy to apply" and preventing bacterial growth both under the adhesive and along the IV tunnel.

In order for adhesive compositions to be utilized in the area of wound/incision closure, a large number of dispensing and packaging systems for cyanoacrylate-based adhesive have been proposed. Example proposals will be discussed seriatim.

U.S. Pat. Nos. 7,306,390 and 6,705,790 issued to Quintero et al. disclose an applicator assembly for dispensing adhesive material having first and second body portions, a frangible ampule container for adhesive, and a breaking member to rupture the container for dispensing the adhesive material.

U.S. Pat. Nos. 6,960,040, 6,494,896, and 6,340,097 to D'Alessio et al. disclose a package assembly suitable for laparoscopic or endoscopic surgery.

U.S. Pat. Nos. 7,128,241, 6,676,322, 6,376,019, 6,322,852, 6,099,807, and 5,928,611 issued to Leung disclose an applicator tip for dispensing cyanoacrylate adhesive stored in a frangible glass ampule container having a porous, absorbent applicator tip that includes a polymerization initiator to accelerate the polymerization of cyanoacrylate adhesive when applied.

U.S. Pat. No. 6,547,467 issued to Quintero discloses a micro-applicator for dispensing and applying cyanoacrylate-based adhesive having a handle portion. A micro-reservoir at the applicator tip holds about 20 microliters or less of adhesive material. The applicator tip may include a spatula, a rolling ball, a grate, a porous material, or a brush.

U.S. Pat. No. 6,779,657 issued to Mainwaring et al. discloses a single-use applicator assembly for applying and dispensing cyanoacrylate monomeric adhesive material comprising a base with at least one sealed container and an applicator tip at least partially disposed in the container such that the tip of the applicator has access to the adhesive material.

U.S. Pat. No. 7,297,217 issued to Dewitt discloses a dispenser for application of a special low viscosity cyanoacrylate adhesive which is used for the manufacture and repair of wooden furniture. The dispenser is provided with a closure member having a metallic pin that penetrates the discharge opening while the closure member is being secured on.

U.S. Pat. No. 4,413,753 issued to Stock discloses a self-draining tip for dispensing cyanoacrylate adhesives that includes a single or segmented, constant-diameter passageway having sharp-edged annular terminations.

U.S. Pat. No. 4,685,591 issued to Schaefer et al. discloses a packaging tube that is suitable for storing and dispensing products containing substantial fractions of cyanoacrylates. The tube sidewall is made of multi-layer sheet material and a covering strip is placed over the inside surface of the tube.

U.S. Pat. No. 5,649,648 issued to Lier et al. discloses a packaging system for free-flowing material such as cyanoacrylate adhesive comprising a container made of an extruded receptacle aluminum that springs back when the pressure is released and a closable applicator point fitted on its outlet aperture.

U.S. Publ. No. 2008/0167681 filed by Stenton discloses an adhesive applicator for applying medical adhesives to surgical incisions having a receiver with: a blunt, deformable cylindrical body and an adhesive-permeable foam material, a frangible ampule containing adhesive material, and a pair of wings having a pressure barb facing toward the cylindrical wall to break the frangible ampule.

U.S. Publ. No. 2008/0105580 filed by Nentwick et al. discloses an applicator tip for dispensing a cyanoacrylate-based adhesive from a reservoir having an offset opening and a distal end. The adhesive material is dispensed when pressure is applied to the applicator tip surface so that the applicator tip is in a deformed configuration.

U.S. Publ. No. 2007/0147947 filed by Stenton et al. discloses an applicator for forming layers of uniform thickness on a substrate surface by: controlling the dispensing of liquid through apertures incorporated within the applicator head, and using a supported thin layer of foam.

U.S. Publ. No. 2006/0282035 filed by Battisti et al. discloses a disposable swab applicator for containing and dispensing cyanoacrylate adhesive which is closed at one end and covered by a swab applicator at the other end. The cyanoacrylate composition is contained by a valve that can be easily opened when desired. The valve can be a ball, a bead, or a capsule. The device can also be heat sterilized using dry heat-sterilization.

All of the example applicator designs are intended for the application of a cyanoacrylate adhesive for the purpose of wound closure. To attain optimal wound closure strength, a thick, even, and consistent layer of cyanoacrylate must be formed over the laceration during application. Therefore, deploying cyanoacrylate onto a laceration is best done if the delivery applicator has a flat surface which can easily be spread across the length of the incision in one unified layer.

All of the example applicator designs are capable of laying down thick beads of adhesive to assist with wound closure. Those same applicators cannot provide the precise drops required, however, to secure a catheter within a body. In order to achieve catheter securement with reduced movement, dislodgement, and unscheduled IV restarting, the cyanoacrylate adhesive needs to be able to be applied directly to the skin at the skin-to-catheter hub interface as well as over the catheter insertion site. Indeed, the application device for the cyanoacrylate needs to be able to reach underneath the catheter hub without causing unnecessary movement to the already-inserted catheter. Due to the curative nature of cyanoacrylate, it is beneficial to be able to apply a small controlled drop or drops for enhanced drying times and overall securement.

As a result, there is a need for an applicator that can easily produce the small controlled drop or drops necessary to secure a catheter while providing optimal catheter-to-skin adhesion strength, hemostasis, and bacterial immobilization at the skin-to-catheter interface. Because the applicator will be used in the medical field, it must also be compatible with sterilization techniques.

BRIEF SUMMARY OF THE INVENTION

This invention discloses an improved applicator design, which is easy to use, suitable for securing catheters, capable of controlling flow rate, and compatible with sterilization techniques. The applicator tapers to a progressively narrow tip that allows the cyanoacrylate to be dispensed with precisely controlled drops. For securement of the catheter hub to the skin, the tapered applicator design allows for easy access to the skin under the hub after the catheter tubing has been inserted. Furthermore, an applicator design, where the tapered applicator tip can be turned onto its side to spread the adhesive drops, in cases where it is deemed necessary by the end user, is advantageous when securing a catheter.

In a non-limiting embodiment, the invention provides an applicator for storing and dispensing an adhesive. The applicator includes a container with walls defining a chamber having an opening at the distal end and fabricated from a material that is substantially impermeable to moisture and air, a frangible seal, and a polymerizable cyanoacrylate monomer adhesive stored in the chamber, a body with a flange having at least one hole, a channel in communication with the hole, extending distally through the body, and having an opening at the distal end, and optionally, a grip capable of constricting the channel when inward pressure is applied to the grip, with the flange being capable of penetrating the frangible seal when the body and the container are compressed together; and a rigid tapered tip in communication with the opening at the distal end of the channel. The applicator may be activated, for example, to release the adhesive from the container, by compressing the body and the container together, and the compressing together of the body and container causes the flange to penetrate the frangible seal, which in turn allows the adhesive to flow into the hole, into and through the channel, and into and out of the rigid tapered tip.

In another non-limiting embodiment, the invention includes a flexible handle comprising a housing for containing a removable adhesive container and a female end of a luer lock at the distal end of the handle, a body comprising a male end of a luer lock at the proximal end of the body and capable of connecting with the female end at the distal end of the handle, and a channel extending distally through the body, and having an opening at the distal end, a rigid tapered tip in communication with the opening at the distal end of the channel, and a removable adhesive container fabricated from a material that is substantially impermeable to moisture and air and capable of fitting within the housing, comprising a frangible seal at the distal end of the container, and a polymerizable cyanoacrylate monomer adhesive stored in the container. The applicator may be activated, for example, to release the adhesive from the container, for example, by compromising (e.g., breaking, tearing, puncturing) the frangible seal. Compromising the seal in turn allows the adhesive to flow into and through the channel, and into and out of the porous tip.

In another non-limiting embodiment, the invention includes a container comprising walls defining a chamber having an opening at the distal end and fabricated from a material that is substantially impermeable to moisture and air, a frangible seal covering the opening, a polymerizable cyanoacrylate monomer adhesive stored in the chamber, and optionally, screw threads on the exterior of the walls, a body comprising a cavity at the proximal end, a channel in communication with the cavity, extending distally through the body, and having an opening at the distal end, a grip capable of constricting the channel when inward pressure is applied to the grip, at least one projection in the cavity, with the projection being capable of penetrating the frangible seal when the body and the container are compressed together. The applicator may be activated, for example, by compressing the body and the container together, including by rotating the body and container about an axis designated by the screw threads (which may be, for example, in a clockwise or counterclockwise direction) thereby compromising (e.g., breaking, tearing, puncturing) the frangible seal. Compromising the seal in turn allows the adhesive to flow into and through the channel, and into and out of the rigid tapered tip.

The design of the current invention ensures that stored liquid sealant can be accurately dispensed and applied to the catheter insertion site, on and underneath the catheter tubing, and underneath the catheter hub. Liquid sealant dispensed by the design of the present invention provides an effective securement of catheters such as intravenous (IV) catheters; peripheral venous catheters (PVCs), central venous catheters (CVCs), peripherally inserted central catheters (PICCs), arterial catheters, urinary catheters, and dialysis catheters.

The present invention provides applicators which are designed to be compatible with irradiation sterilization techniques such as gamma sterilization, electron beam sterilization, and x-ray sterilization so that adhesive stored in the applicators can be sterilized by irradiation sterilization. Because of their exceptional barrier properties, the materials used for the adhesive container are suitable for storing and sterilizing cyanoacrylate-based adhesives in accordance with the present invention. The adhesives packaged in the applicators are therefore able to be sterilized by irradiation sterilization techniques, and are not cured upon sterilization. More desirably, the adhesive packaged in the applicators disclosed in the present invention provides a long-term shelf life stability of at least 12 months, and more preferably of at least 24 months after sterilization by irradiation sterilization techniques.

It is to be understood that both the foregoing general description and the following detailed description are exemplary, but are not restrictive, of the invention.

BRIEF DESCRIPTION OF THE DRAWING

The invention is best understood from the following detailed description when read in conjunction with the accompanying drawing. It is emphasized that, according to common practice, the various features of the drawing are not to scale. On the contrary, the various features are arbitrarily expanded or reduced for clarity. Included in the drawing are the following figures.

DESCRIPTION OF THE INVENTION

This invention relates to dispensers and/or applicators for storing, sterilizing, and applying an adhesive or sealant material such as a polymerizable cyanoacrylate monomer. The applicators are designed to be safe and easy to use, with a tapered tip and the ability to control the flow rate of an adhesive or sealant material for the purpose of precise control. The applicator is also compatible with radiation sterilization techniques. In particular, the containers for the adhesive and sealant material of the applicators are made of materials with high moisture and air barrier properties such as cyclic olefin copolymers or acrylonitrile copolymers so that the adhesive and sealant material can be sterilized by radiation and thereafter provide long-term shelf stability.

In a non-limiting embodiment the present invention includes: a body, a container for containing an adhesive material, and a rigid tapered tip. Adhesives may be pre-packaged in the applicator in the container, for example, sealed within the container by a frangible foil or a membrane, which may be hermetically sealed. The container for adhesives can be fabricated from a multi-layer sheet material, and the inner layer of the container, which contacts the adhesive, can be fabricated from a cyclic olefin copolymer. The container thereby constructed is compatible with radiation sterilization, such as electron beam, gamma, or x-ray sterilization, so that adhesives inside the applicator can be sterilized via radiation without diminished shelf stability (e.g., without prematurely polymerizing). The long-term shelf life stability of adhesive packaged in the applicators may be provided after radiation sterilization.

Figure 1:
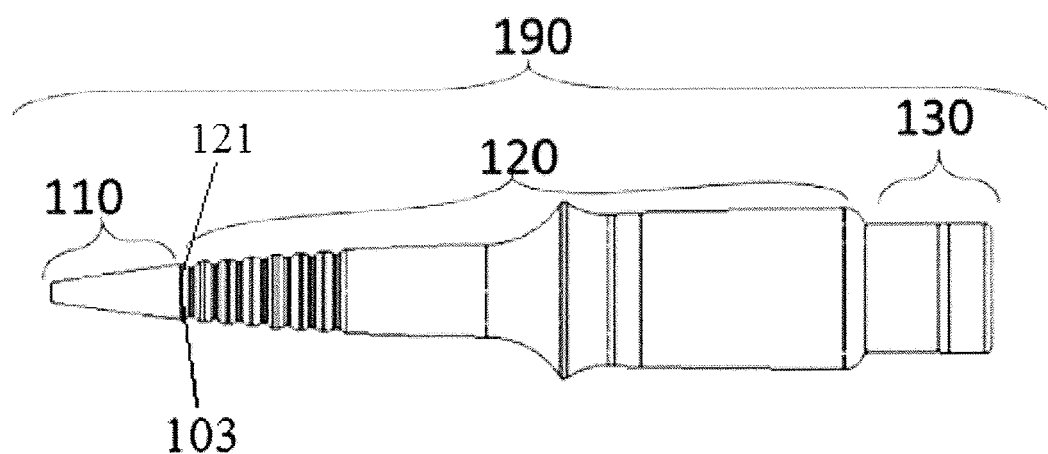
FIG. 1 is a perspective view of a first exemplary applicator of this invention.
Figure 2:
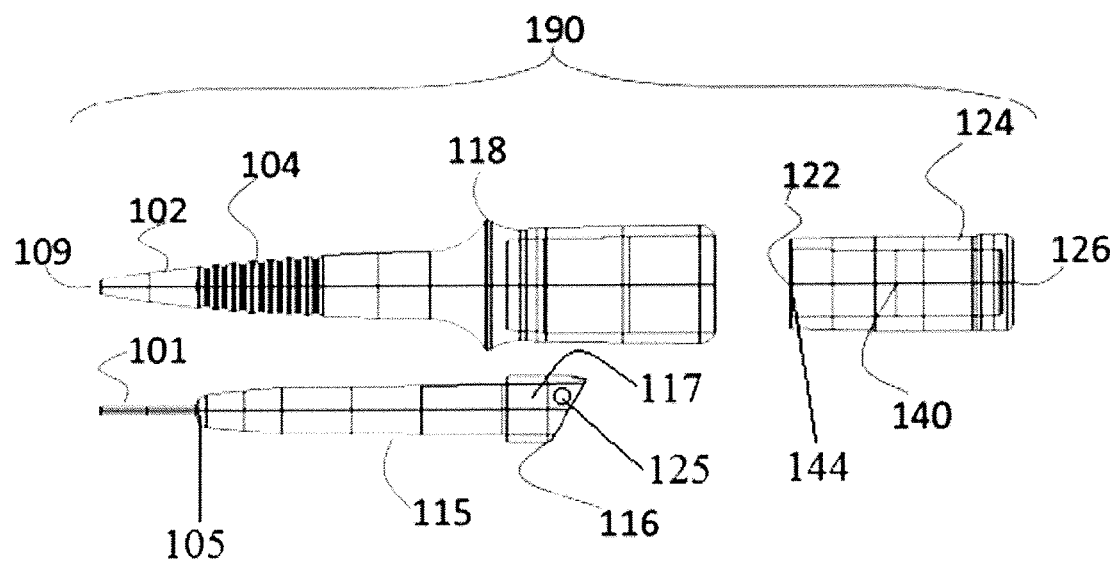
FIG. 2 is an exploded view of the exemplary embodiment of FIG. 1.
Figure 3:
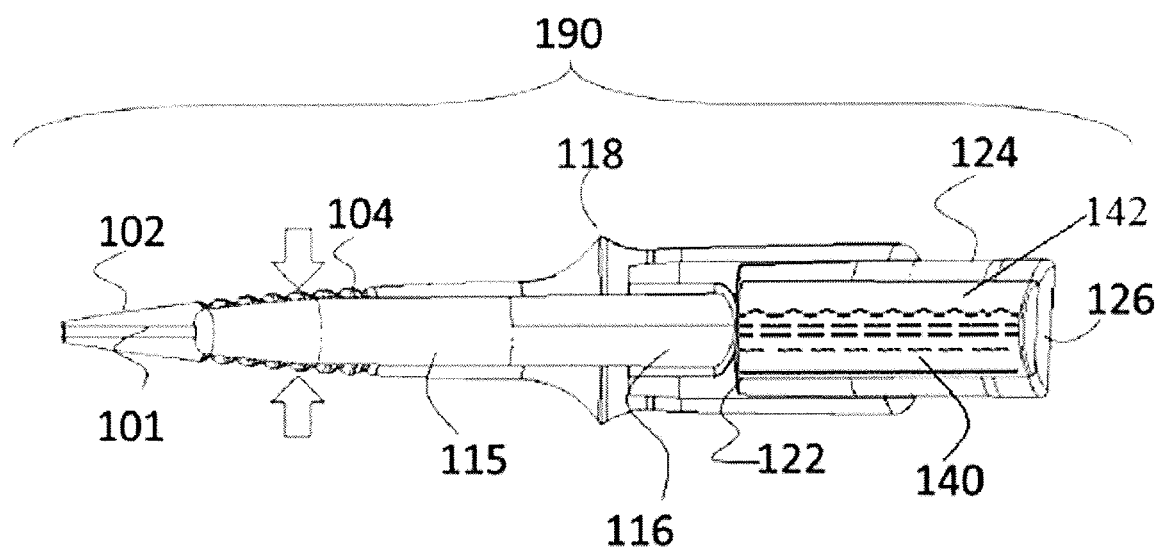
FIG. 3 is a cross-sectional view of the exemplary embodiment of FIG. 1.

FIGS. 1-3 illustrate one non-limiting embodiment of the invention. As shown in FIG. 1, the applicator 190 includes a rigid tapered applicator tip 110, an applicator body 120, and a container 130.

FIGS. 2 and 3 show an exploded view and a cross-sectional view of the first embodiment of the applicator 190, respectively. The applicator body 120 has a distal end 121, and this distal end 121 connects to the proximal end 103 of the applicator tip 110. The applicator body 120 may include a flow restrictor 105, a grip 104, a flange 117 which has at least one hole 125, and a channel 115 having an opening 109 at its distal end, as shown in FIGS. 2 and 3. The hole 125 and the channel 115 are in communication and serve to have access to, and as a conduit for, the adhesive 140 stored in the container 130.

The container 130 comprises a plurality of walls 124 that define a chamber 142 that is preferably open at the distal end 144, which may be closed off by at least one seal, for example, a frangible seal 122 as shown in the cross-sectional view in FIG. 3. The wall 124 is present at the proximal end 126 of the container 130.

In order to activate the applicator 190, the applicator container 130 may be moved by a user toward the applicator body 120. For example, a user may push downward on the proximal end 126 of the wall 124 of the container 130 with a finger or thumb, while the user holds the applicator 190 in a hand. Once the container 130 and the body 120 are pushed together, the hole 125 is pushed beyond the frangible seal 122 and moved into the container 130 so that the adhesive 140 can flow through the hole 125, into the channel 115, and through the opening 109 at the distal end of the channel 115. As the adhesive 140 exits the rigid applicator tip 110, the user may apply the adhesive 140 to a desired surface.

The release/dispense mechanism is not limited to the specific embodiment shown in FIGS. 1-3. The hole 125 and the channel 115 can be in different positions. The relative positioning of the hole 125 to the seal 122 can be designed using other suitable mechanisms.

Tapered Tip

The applicator tip 110 is rigid to allow for precise application of the adhesive 140. Furthermore, the tip 110 has a tapered outer surface 102 which may allow it to more easily slide underneath a catheter. In order for the applicator tip 110 to deliver a precise amount of the adhesive 140 and control the flow of the adhesive 140, a tip channel 101 is designed within the applicator tip 110. The diameter of the opening 109 and tip channel 101 within the applicator tip 110 is in the range of about 0.005 mm to 3 mm, preferably about 0.01 mm to 3 mm, preferably about 0.02 mm to 3 mm, preferably about 0.05 mm to 3 mm, and more preferably about 0.1 mm to 2 mm. Furthermore, the tip channel 101 may be tapered. Such a tapering of the tip channel 101 may provide resistance to the flow of the adhesive 140.

Body

The applicator body 120, including the flange 117, the grip 104, and the channel 115, may be fabricated from any suitable materials. In preferred aspects, the applicator body 120 and channel 115 are made of a material that can prevent or reduce the premature polymerization of the adhesive 140 flowing through the channel 115. Suitable materials include, but are not limited to, high density polyethylene (HDPE), medium density polyethylene (MDPE), low density polyethylene (LDPE), polypropylene, polyvinylchloride, polycarbonate, polytetrafluoroethylene (PFTE), polyethylene terephthalate (PET), polystyrene (PS), and polymethylpentene. The grip 104 and the channel 115 are preferably flexible.

Grip

The grip 104 of the applicator body 120 allows a user to conveniently hold and position the applicator 190 during use. For example, a user may hold the grip 104 similar to how a pen is held, between the thumb and one or more fingers. The grip 104 may itself be comprised of a flexible material that allows the user to squeeze the grip 104 inward, or may comprise the flow restrictor 105 that the user may be able to squeeze, move, or adjust inward toward the channel 115. Constricting the grip 104 or the flow restrictor 105 may in turn constrict the channel 115 or the tip channel 101, which itself may be comprised of a flexible material, in order to control the flow of the adhesive 140 through the channel 115. The flow rate of the adhesive 140 may be controlled, for example, by the user providing a desired amount of pressure on the grip 104 or the flow restrictor 105 of the applicator body 120. A desired amount of adhesive 140 can thus be dispensed by applying a desired amount of force to the flow restrictor 105 or grip 104.

Control of Adhesive Flow Rate

The flow rate of adhesive 140 may be controlled by providing a constant but slow pressure on the griping section 104 of the applicator body 120. The flow resister 105 may be included at the junction of the tip 110 and the body 120. The flow resister 105 may take the form of a tapering of the channel 115, a tapering of the tip channel 101, or a porous material. In certain embodiments, a desired amount of the adhesive 140 can be dispensed by applying a desired force to the grip 104. The rigid tapered tip 110 in combination with the grip 104 can ensure the precise application of securement adhesive to the catheter insertion site.

Cutting Portion

A cutting portion 116 is designed to be sharp and strong so as to readily break the frangible seal 122 for dispensing adhesive 140 inside the container 130. Conversely, the grip section 104 should be flexible and soft enough to make squeezing readily possible. Therefore, the material of the applicator body 120 is specifically designed for the applicator body 120. Suitable materials for the applicator body 120 include but are not limited to polyethylene (PE), polypropylene, polyvinylchloride, polycarbonate, polytetrafluoroethylene (PFTE), polyethylene terephthalate (PET), polystyrene (PS), and polymethylpentene with a certain percentage of thermoplastic elastomers (TPE). TPE may be present in the materials used for constructing the applicator body 120 in the amount of 5% to 60%, preferably 5% to 50%, and more preferably 5% to 40%. Without including TPE, the applicator body 120 is too hard to be squeezed to dispense and control the flow of the adhesive 140. If too much TPE is present in the applicator body 120, the cutting portion 116 becomes too soft to puncture through the frangible seal 122 for dispensing adhesive 140 inside the container 130.

Container Volume

The adhesive container 130 has a volume of about 0.05 mL to 20 mL, preferably about 0.05 mL to 15 mL, and more preferably about 0.1 mL to 10 mL. In order to inhibit the premature polymerization of the adhesive 140, the volume of the applicator 190 is preferably about 20 to 80 percent, and more preferably 30 to 80 percent, filled by the adhesive 140.

Finger Stopper

In order to enhance comfort and enable the user to hold and activate the applicator 190, a finger stopper 118 is added to the applicator body 120, as shown in another cross-sectional view of the applicator design of the present invention (FIG. 3). The user may use their index and middle fingers to hold the finger stopper 118, while using their thumb to push the proximal end 126 of the container 130 and activate the applicator 190.

Frangible Seal

The frangible seal 122 is heat sealed to the container 130 for storing the adhesive 140. Suitable materials for the frangible seal 122 may include, but are not limited to, aluminum foil, plastic membrane, laminated aluminum foil, plastic wrap, waxed paper, oiled paper, or the like. Laminated aluminum foil may be composed of at least two layers of different materials which include, but are not limited to, aluminum, acrylonitrile copolymer, low density polyethylene, low density polypropylene, polyethylene teraphthalate, cyclic olefin copolymer, and the like. In a preferred embodiment, cyclic olefin copolymer or acrylonitrile copolymer as the inner layer is used to construct the frangible seal 122.

Container Materials

Suitable materials for the container 130 should have a desired barrier property for moisture and air so that the premature polymerization of the adhesive 140 can be prevented or inhibited. Suitable materials for the container 130 include, but are not limited to, high density polyethylene (HDPE), polypropylene, polyvinylchloride, acrylonitrile copolymer, polycarbonate, polytetrafluoroethylene (PFTE), cyclic olefin copolymer, polyethylene terephthalate (PET), and the like. In a preferred embodiment, the container 130 is made of multi-layer sheet material with cyclic olefin copolymer as the inner layer. In another preferred embodiment, the container 130 is made of multi-layer sheet material with acrylonitrile copolymer as the inner layer. In another preferred embodiment, the entire container 130 is made of cyclic olefin copolymer except the frangible foil. In another preferred embodiment, the entire container 130 is made of acrylonitrile copolymer except the frangible foil.

Suitable materials for the container 130 and the inner layer of the frangible seal 122 include unsaturated cyclic monomers and one or more unsaturated linear monomer. Unsaturated linear monomers include without limitation alkenes having 1 to 20, preferably from 1 to 12 carbon atoms, most preferably from 1 to 6 carbon atoms, such as for example alpha-olefins, for example ethylene, propylene, and butylene. Unsaturated cyclic monomers include without limitation, cyclopentadiene and derivatives thereof such as for example dicyclopentadiene and 2,3-dihydrocyclopentadiene; 5,5-dimethyl-2-norbornene, 5-butyl-2-norbornene, 5-ethylidene-2-norbornene, norbornene and derivatives thereof, 2-norbornene, 5-methyl-2-norbornene, 5-methoxycarbonyl-2-norbornene, 5-cyano-2-norbornene, 5-methyl-5-methoxycarbonyl-2-norbornene, and 5-phenyl-2-norbornene, and combinations of two or more thereof. Other unsaturated linear monomers may be chosen from 1-butene, 4-methyl-1-pentene, 1-hexene, 1-octene, 1-decene, 1-dodecene, 1-tetradecene, 1-hexadecene, 1-octadecene and 1-eicocene, cydopentene, cydohexane, 3-methylcyclohexene, cyclooctene, 1,4-hexadiene, 4-methyl-1,4-hexadiene, 5-methyl-1,4-hexadiene, 1,7-octadiene, di cyclopentadiene, 5-ethylidene-2-norbornene, 5-vinyl-2-norbornene, tetracyclododecene, 2-methyltetracyclododecene, and 2-ethyltetracyclododecene; or combinations of two or more thereof. Preferably the unsaturated linear monomer is 1-hexene, butylene, propylene, and ethylene. Preferably the copolymer is cyclopentadiene-ethylene copolymer, cyclopentadiene-butylene copolymer, cyclopentadiene-hexene copolymer, cyclopentadiene-propylene copolymer, cyclopentadiene-octene copolymer, di cyclopentadiene-ethylene copolymer, dicyclopentadiene-butylene copolymer, dicyclopentadiene-hexene copolymer, dicyclopentadiene-propylene copolymer, di cyclopentadiene-octene copolymer, norbornene-ethylene copolymer, norbornene-propylene copolymer, norbornene-butylene copolymer, norborene-hexene copolymer, 5-cyano-2-norbornene-ethylene copolymer, 5-cyano-2-norbornene-propylene copolymer, 5-cyano-2-norbornene-butylene copolymer, 5-phenyl-2-norbornene-ethylene copolymer, 5-phenyl-2-norbornene-propylene copolymer, 5-phenyl-2-norbornene-butylene copolymer, 5-methyl-5-methoxycarbonyl-2-norbornene-ethylene copolymer, 5-methyl-5-methoxycarbonyl-2-norbornene-propylene copolymer, 5-methyl-5-methoxycarbonyl-2-norbornene-butylene copolymer, 5-ethylidene-2-norbornene-ethylene copolymer, 5-ethylidene-2-norbornene-propylene copolymer, and 5-ethylidene-2-norbornene-butylene copolymer, acrylonitrile copolymers produced by polymerizing a major proportion of a monounsaturated nitrile and a minor proportion of another monovinyl monomer or indene copolymerizable nitrile polymers produced by polymerizing a major portion of a monounsaturated nitrile and a minor portion of another monovinyl monomer or indene copolymerizable therewith in the presence of a diene rubber, polyacarylates, polymethoactrylate, polyalkyl methacrylates, polyethers, polysiloxanes, polysulfones, polyphenylene sulfide, polyether ether ketones, thermoplastic polyimides, polybenzimidazoles, polyquinoxalones, polyoxazolines, styrene-acrylonitrile copolymer and acrylonitrile-butadiene-styrene copolymer, vinyl acetate containing polymers, maleic anhydride containing polymers, butadiene and/or isoprene based elastomers, acrylonitrile, and methacrylonitrile.

Preferred materials used to construct the container 130 provide high barrier properties which ensure the stability of the cyanoacrylate adhesive 140 stored in the container 130. The exceptional barrier properties offered by preferred materials of this invention make them ideal materials for use in construction of the packaging bodies in accordance with the present invention. Preferred materials of this invention offer a high barrier to oxygen at all levels of relative humidity. This ensures that a consistently high barrier to oxygen is maintained, regardless of the humidity of the surrounding environment. In addition, the water vapor barrier properties of the preferred materials of this invention make them desirable materials for packaging and sterilizing cyanoacrylate-based adhesive materials in accordance with the present invention.

The container 130, which is preferably removable, may comprise a cyclic olefin copolymer or an acrylonitrile copolymer. The container 130 may comprise a single layer of a cyclic olefin copolymer or an acrylonitrile copolymer, or may comprise a plurality of layers, whereby the cyclic olefin copolymer or an acrylonitrile copolymer comprises the inner-most layer of the container 130 such that the cyclic olefin copolymer layer or an acrylonitrile copolymer contacts the adhesive 140 stored in the container 130. The container 130 may be a stick pack container. The frangible seal 122 may comprise a foil, for example, aluminum foil, and may be laminated with a cyclic olefin copolymer or an acrylonitrile copolymer.

Medical Articles that can be Secured

Medical articles that can utilize the liquid sealant dispensed by the design of the present invention include, but are not limited to, connector fittings, catheter systems (e.g., including catheters, catheter hubs, catheter adaptors, catheter tubing, etc.), fluid supply lines, inserted ports, other similar articles, or combinations thereof. Examples of catheter systems can include, but are not limited to, intravenous (IV) catheters; peripheral venous catheters (PVCs), central venous catheters (CVCs), peripherally inserted central catheters (PICCs), arterial catheters, urinary catheters, and dialysis catheters. Exemplary vascular access devices include both straight and ported intravenous catheters such as the AUTOGUARD™ shielded catheter commercially available from Becton, Dickinson, and Company, integrated peripheral intravenous catheters, winged needle sets, and blood collections sets. An IV access set, such as the BD NEXIVA™ Closed Intravenous (IV) Catheter System commercially available from Becton, Dickinson, and Company may also be used to create a closed access system. In order to keep the catheter, tubing, or other medical line properly positioned for the duration of treatment, the catheter, tubing, or medical line can be secured to the patient with the liquid sealant dispensing from the applicator 190, which is simple to use while providing reliable fixation of the catheter to the skin of the patient.

The special design of the current invention ensures that the liquid sealant stored in the applicator 190 can be accurately dispensed and applied to the catheter insertion site, on and underneath the catheter tubing, and underneath the catheter hub, which conventional catheter dressing products cannot achieve. Liquid sealant dispensed by the applicator 190 provides an effective securement of catheters such as intravenous (IV) catheters; peripheral venous catheters (PVCs), central venous catheters (CVCs), peripherally inserted central catheters (PICCs), arterial catheters, urinary catheters, and dialysis catheters. Compared to conventional and commercially available catheter dressing products, which include, but are not limited to, the Tegaderm™, Opsite, HubGuard®, and Durapore products, liquid sealant dispensed by the applicator 190 provides a much stronger adhesion strength in terms of catheter securement. As an example, the average adhesion strength for securing a BD Autoguard catheter by the liquid sealant stored in the applicator 190 at 30 minutes after application is about 4 times stronger than that of the Opsite product. The average adhesion strength for securing a BD Nexiva catheter by the liquid sealant stored in the applicator 190 at 30 minutes after application is about 9 times stronger than that of the Hubguard® product.

Adhesive Properties

Besides securing the catheter, the liquid sealant stored in the applicator 190 provides hemostasis. The in vitro tests demonstrated that liquid sealant stored in the applicator 190, achieved consistent inhibition of blood flow and rapid modified activated clotting times. Liquid sealant stored in the applicator 190 achieved hemostasis twelve-fold faster than thromboplastin in the mACT assay. In an in vivo study conducted on heparinized swine, the liquid sealant stored in the applicator 190 demonstrated hemostatic properties statistically equivalent to that of currently marketed and approved hemostatic products, including the Gelfoam® Powder and Kaltostat® products, and is significantly more effective when compared to the untreated sham control.

The liquid sealant composition of the present invention has also been shown to immobilize bacteria in in vitro studies with gram+ and gram− bacteria and fungi including MRSA, *Staphylococcus epidermidis, Pseudonomas aeruginosa, Candida albicans*, and *Corynebacterium pseudodiptheriticum*, to prevent those inadvertently introduced from migrating into the catheter insertion site.

The liquid sealant composition of the present invention has been proven to be a moisture barrier, which effectively seals the catheter insertion site. The liquid sealant stored in the applicator 190 has shown significant resistance to water penetration tested by the hydrostatic pressure impact test. The liquid sealant composition stored in the applicator 190 provides an effective barrier against aqueous solutions, and the sealant integrity of the adhesive film layer once applied to the catheter stays intact with no pinholes. The water-based liquid dye did not penetrate the adhesive film at the junction of the catheter and the skin; therefore, the liquid sealant composition stored in the applicator 190 provides securement to the catheter while providing a proficient sealant layer for the insertion site as well as the catheter hub.

Adhesive Composition

The applicator 190 of the present invention is used to apply liquid sealant to secure catheters on human skin. Preferred liquid sealants are readily polymerizable, e.g., anionically polymerizable and/or free radical polymerizable. The adhesive 140 is preferably a 1,1-disubstituted ethylene monomer, e.g., a cyanoacrylate monomer. In a preferred embodiment, the adhesive 140 that is packaged in the applicator 190 is based upon one or more polymerizable cyanoacrylate monomers, and/or reactive oligomers of cyanoacrylate. Such cyanoacrylate monomers are readily polymerizable, e.g., anionically polymerizable and/or free radical polymerizable, to form polymers. Cyanoacrylate monomers suitable for use in accordance with the present invention include, but are not limited to, 1,1-disubstituted ethylene monomers of the formula:

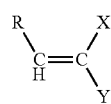
(Formula I)

wherein X and Y are each strong electron withdrawing groups, and R is H, —CH=CH$_2$, or a C$_1$-C$_4$ alkyl group. Examples of monomers within the scope of Formula I include alpha-cyanoacrylates, vinylidene cyanides, C$_1$-C$_4$ alkyl homologues of vinylidene cyanides, dialkyl methylene malonates, acylacrylonitriles, vinyl sulfinates and vinyl sulfonates of the formula CH$_2$=CX'Y wherein X' is —SO$_2$R' or —SO$_3$R' and Y' is —CN, —COOR', —COCH$_3$, —SO$_2$R' or —SO$_3$R', and R' is H or hydrocarbyl. Preferred monomers of Formula I for use in this invention are alpha-cyanoacrylates. These monomers are known in the art and have the formula:

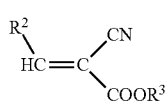
(Formula II)

wherein R$^2$ is hydrogen and R$^3$ is a hydrocarbyl or substituted hydrocarbyl group; a group having the formula —R$^4$—O—R$^5$—O—R$^6$, wherein R$^4$ is a 1,2-alkylene group having 2-4 carbon atoms, R$^5$ is an alkylene group having 2-12 carbon atoms, and R$^6$ is an alkyl group having 1-6 carbon atoms; or a group having the formula:

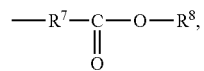

wherein R$^7$ is:

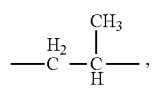

or —[C(CH$_3$)$_2$]$_n$ wherein n is 1-14, preferably 1-8 carbon atoms and R$^8$ is an organic moiety.

Examples of suitable hydrocarbyl and substituted hydrocarbyl groups include straight chain or branched chain alkyl groups having 1-16 carbon atoms; straight chain or branched chain C1-C16 alkyl groups substituted with an acyloxy group, a haloalkyl group, an alkoxy group, a halogen atom, a cyano group, or a haloalkyl group; straight chain or branched chain alkenyl groups having 2 to 16 carbon atoms; straight chain or branched chain alkynyl groups having 2 to 12 carbon atoms cycloalkyl groups; arylalkyl groups; alkylaryl groups; and aryl groups.

The organic moiety R$^8$ may be substituted or unsubstituted and may be a straight chain, branched, or cyclic, saturated, unsaturated, or aromatic. Examples of such organic moieties include C1-C8 alkyl moieties, C2-C8 alkenyl moieties, C2-C8 alkynyl moieties, C3-C12 cycloaliphatic moieties, aryl moieties such as phenyl and substituted phenyl, and arylalkyl moieties such as benzyl, methylbenzyl, and phenylethyl. Other organic moieties include substituted hydrocarbon moieties, such as halo (e.g., chloro-, fluoro-, and bromo-substituted hydrocarbons) and oxy- (e.g., alkoxy substituted hydrocarbons) substituted hydrocarbon moieties. Preferred organic radicals are alkyl, alkenyl and alkynyl moieties having from 1 to about 8 carbon atoms, and halo-substituted derivatives thereof. Particularly preferred are alkyl moieties of 4 to 8 carbon atoms. In the cyanoacrylate monomer of Formula II, R$^8$ is preferably an alkyl group having 1-10 carbon atoms or a group having the formula -AO R$^9$, wherein A is a divalent straight or branched chain alkylene or oxyalkylene moiety having 2-8 carbon atoms, and R$^9$ is a straight or branched alkyl moiety having 1-8 carbon atoms. The preferred alpha-cyanoacrylate monomers used in this invention are 2-octyl cyanoacrylate, dodecyl cyanoacrylate, 2-ethylhexyl cyanoacrylate, butyl cyanoacrylate, methyl cyanoacrylate, 3-methoxybutyl cyanoacrylate, 2-butoxyethyl cyanoacrylate, 2-isopropoxyethyl cyanoacrylate, or 1-methoxy-2-propyl cyanoacrylate, or a combination thereof.

Manufacture of Adhesive

In preferred embodiments of the present invention, the cyanoacrylate monomers can be prepared according to methods known in the art. Reference is made, for example, to U.S. Pat. Nos. 2,721,858 and 3,254,111, each of which is hereby incorporated in its entirety by reference. One such process includes, for example, reacting a cyanoacetate with formaldehyde in the presence of a basic condensation catalyst at an elevated temperature to produce a low molecular weight polymer. A de-polymerization (or cracking) step is followed under high temperature and high vacuum in the presence of acidic and anionic inhibitors, yielding a crude monomer that can be distilled under high temperature and high vacuum in the presence of radical and acidic inhibitors.

Bioabsorbablity of Adhesive

The liquid sealant that may be packaged in the applicator 190 may be bioabsorbable. The term bioabsorbable refers to polymers or medical devices that are able to completely degraded, eroded, and/or gradually absorbed or eliminated by the body when such polymers or medical devices are exposed to body fluid such as blood. The bioabsorbable adhesives can be used in many different applications including but not limited to general wound closure, endoscopic surgery, cardiac surgery, hernia surgery, and arthroscopic surgery. Bioabsorbable adhesives are preferably based on cyanoacrylates. In embodiments of the present invention, a bioabsorbable adhesive composition is composed of alkoxyalkyl cyanoacrylate and polyethylene glycol. The bioabsorbable adhesive compositions can also consist of the mixture of alkyl cyanoacrylate, alkoxyalkyl cyanoacrylate, and polyethylene glycol. A preferred alkoxyalkyl cyanoacrylate is methoxyisopropyl cyanoacrylate. Other bioabsorbable adhesives may include copolymers of alkyl cyanoacrylate or alkoxyalkyl cyanoacrylate with other biocompatible monomers such as trimethylene carbonate, alkylene glycol, glycolide, lactide, ε-caprolactone, and dioxane.

The adhesive may be bioabsorbable or non-bioabsorbable. Non-limiting examples of suitable adhesives include 2-octyl cyanoacrylate, dodecyl cyanoacrylate, 2-ethylhexyl cyanoacrylate, butyl cyanoacrylate, methyl cyanoacrylate, 3-methoxybutyl cyanoacrylate, 2-butoxyethyl cyanoacrylate, 2-isopropoxyethyl cyanoacrylate, 1-methoxy-2-propyl cyanoacrylate, or a combination thereof. 2-octyl cyanoacrylate and n-butyl cyanoacrylate are non-limiting examples of non-bioabsorbable adhesives.

Sterilization Techniques

The applicator 190 disclosed herein is compatible with irradiation sterilization techniques such as electron beam sterilization, gamma sterilization, and/or x-ray sterilization. The preferred materials for the applicator 190 are irradiation stable under the maximum dosage of e-beam, gamma, and x-ray sterilization. The exceptional barrier properties offered by preferred materials make it an ideal inner layer material for use in construction of packaging bodies, in accordance with the present invention, to sterilize adhesive compositions using irradiation sterilization techniques. The inner layer made of the preferred materials provides high barrier properties which ensure the stability of the liquid adhesive compositions stored in the applicator 190. Preferred materials used to construct the liquid container 130 offer a high barrier to oxygen at all levels of relative humidity. This ensures that a consistently high barrier to oxygen is maintained, regardless of the humidity of the surrounding environment. In addition, the water vapor barrier properties of the preferred materials are comparable to other plastic packaging materials and are ultimately enhanced by the outer layer secured thereto in accordance with the present invention. All of the properties of the preferred materials enable them to be suitable materials as the package body for sterilizing cyanoacrylates via an irradiation sterilization technique.

The dose of irradiation applied should be sufficient to sterilize both the applicator 190 and the adhesive 140 inside. In certain embodiments, the e-beam irradiation can be in a suitable dosage of from about 5 to 50 kGy, preferably from about 10 to about 30 kGy, and more preferably from about 12 to about 25 kGy. The dose of x-ray applied to the adhesive 140 stored in the applicator 190 is in the range of 5 kGy to 40 kGy, preferably in the range of about 5 kGy to 30 kGy, more preferably about 5 kGy to 25 kGy. Gamma irradiation for the adhesive 140 packaged in the applicator 190 can be in a suitable dosage from about 5 to 50 kGy, preferably about 5 to about 40 kGy, and more preferably from about 5 to 25 kGy.

Adhesive Shelf-Life

The adhesive 140 stored in the applicator 190 is not cured or polymerized upon e-beam, gamma, or x-ray sterilization. In more preferred embodiments, the adhesive materials provide a stable shelf life for use in the medical field. For example, the adhesive 140 in the applicator 190 after irradiation sterilization may provide a shelf life of at least 12 months, more preferably at least 24 months. The shelf life stability of the liquid adhesive compositions in various the applicator 190 sterilized by different irradiation sterilization techniques may be evaluated by an accelerated aging study at 80° C. The study is performed in an oven at 80° C. for a period of 13 days. Based on ASTM F1980, 13 days accelerated aging at 80° C. correlates to 2 years of shelf life at ambient temperatures, and 1 day of accelerated aging at 80° C. is equal to 56 days at ambient temperature.

The liquid sealant is capable of being stored in the applicator 190 at room temperature (e.g., about 20° C. to about 25° C.) for long periods of time without substantially increasing in viscosity, deteriorating, degrading, polymerizing, or otherwise reacting or changing in properties. The shelf life of a product may be evaluated by any suitable technique. For example, the applicator 190 may undergo an accelerated aging test at elevated temperature to evaluate the shelf life stability of the cyanoacrylate compositions. This test can be performed in an oven at 80° C. for a period of 13 days. Based on ASTM F1980, 13 days accelerated aging at 80° C. correlates to 2 years of shelf life at ambient temperatures. Similarly, real time shelf life studies could also be conducted. At the end of 2 years of shelf life evaluated by real time studies or accelerated aging studies, cyanoacrylate compositions in the applicator 190 sterilized by an irradiation method preferably have a viscosity of less than about 400 cPs, more preferably less than about 300 cPs, and most preferably less than about 200 cPs.

The cyanoacrylate compositions stored in the applicator 190 can provide a shelf life of at least 24 months under an irradiation technique such as gamma. This was confirmed by an accelerated aging test by storing the sterilized package containing a sterilized cyanoacrylate composition at 80° C. for 13 days. In comparison, however, the same cyanoacrylate adhesive compositions contained in other package systems made of only low density polyethylene (LDPE), high density polyethylene (HDPE), and polypropylene, amber HDPE, glass, and polyethylene terephthalate glycol were not found to be as stable upon irradiation sterilization. The cyanoacrylate compositions packaged in other systems as listed above were cured in about a month after the irradiation sterilization, exhibiting an unacceptable shelf life. The cyanoacrylate compositions packaged in the applicator 190 provide the extended shelf life of at least two years after irradiation sterilization. These observations demonstrate the uniqueness of the applicator 190 as a suitable container for the cyanoacrylate compositions.

Adhesive Filtering and Sterility Assurance Level

In order to reduce the bioburden, the cyanoacrylate adhesive compositions stored in the applicator 190 may be filtered through a 0.2 μm filter prior to different irradiation sterilizations. A sterility assurance level (SAL) should be obtained at a minimum of $10^{-3}$, which means that the probability of a single unit being non-sterile after sterilization is 1 in 1000. In more preferred embodiments, the sterility assurance level may be at least $10^{-6}$. The sterility of the cyanoacrylate adhesives packaged in various applicators 190 after irradiation sterilization may be analyzed by bacteriostasis and fungistasis tests. After testing with challenging microorganisms such as *Bacillus subtilis, Candida albicans*, and *Aspergillus niger*, no growth of the microorganisms for the cyanoacrylate adhesive in the applicator 190 after irradiation sterilization indicates the sterility of the cyanoacrylate adhesive.

Stabilizing Agent

The cyanoacrylate monomers may be stabilized by using a combination of free radical and anionic stabilizers before storing into the various applicator 190 of the present invention. Suitable free radical stabilizers include, without limitation, butylated hydroxy anisole (BHA); hydroquinone; catechol; hydroquinone monomethyl ether and hindered phenols such as butylated hydroxyanisol; 4-ethoxyphenol; butylated hydroxytoluene (BHT, 2,6-di-tert-butyl butylphenol), 4-methoxyphenol (MP); 3methoxyphenol; 2-tert-butyl-4methoxyphenol; and 2,2-methylene-bis-(4-methyl-6-tert-butylphenol). The stabilizers may be present in an amount of 200 ppm to 20,000 ppm, preferably 300 ppm to 20,000 ppm, and more preferably 300 ppm to 15,000 ppm.

Suitable anionic stabilizers for adhesives 140 stored in various applicators 190 may include, but are not limited to, perchloric acid, hydrochloric acid, hydrobromic acid, sulfur dioxide, toluenesulfonic acid, fluorosulfonic acid, phosphoric acid, ortho, meta, or para-phosphoric acid, trichloroacetic acid, and sulfuric acid. The anionic stabilizer may be present in an amount of about 2 ppm to about 500 ppm, preferably about 10 ppm to about 200 ppm.

Colorants

In certain embodiments, the cyanoacrylate adhesive in the applicator 190 may further contain small amounts of colorants such as dyes or pigments. Suitable dyes include derivatives of anthracene and other complex structures, specifically, without limitation, 1-hydroxy-4-[4-methylphenylamino]-9,10 anthracenedione (D&C violet No. 2); 9-(o-carboxyphenyl)-6-hydroxy-2,4,5,7-tetraiodo-3H-xanthen-3-one-disodium salt, monohydrate (FD&C Red No. 3); disodium salt of 6-hydroxy-5-[(4-sulfophenyl)axo]-2-naphthalene-sulfonic acid (FD&C Yellow No. 6); 2-(1,3dihydro-3-oxo-5-sulfo-2H-indole-2-ylidine)-2,3-dihydro-3-oxo-1H-ind-ole-5 sulfonic acid disodium salt (FD&C Blue No. 2); and 1,4-bis(4-methylanilino)anthracene-9,10-dione (D&C Green No. 6). The preferred dyes are D&C Violet No. 2, FD&C Blue No. 2, and D&C Green No. 6.

Accelerators

A polymerization accelerator may be included in the cyanoacrylate adhesive materials stored in the applicator 190 disclosed herein. Suitable polymerization accelerators may include, but are not limited to, calixarenes and oxacalixarenes, silacrowns, crownethers, cyclodextrin and its derivatives, polyethers, aliphatic alcohol, various aliphatic carboxylic acid esters, benzoyl peroxide, amine compounds such as are triethyl amine, diethyl amine, butyl amine, isopropyl amine, tributyl amine, N,N,-dimethyl aniline, N,N-diethyl aniline, N,N-dimethyl-p-toluidine, N,N-dimethyl-m-toluidine, N,Ndimethyl-o-toluidine, dimethyl benzyl amine, pyridine, picoline, vinyl pyridine, ethanolamine, propanolamine and ethylene diamine, quaternary ammonium salts such as alkyl ammonium salts, amide-bonded ammonium salts, ester-bonded ammonium salts, ether-bonded ammonium salts and alkylimidazolinium salts, cyclosulfur compounds and derivatives, and polyalkylene oxides and derivatives. The polymerization accelerator may be present in an amount less than about 1,000 ppm, and preferably less than about 500 ppm.

Plasticizing Agent

The cyanoacrylate adhesive 140 in the applicator 190 may optionally include at least one plasticizing agent that imparts flexibility to the polymer formed from the monomer. The plasticizing agent preferably does not contain any moisture and should not adversely affect the stability of the cyanoacrylate compositions. Examples of suitable plasticizers include, but are not limited to, tributyl citrate (TBC), acetyl tributyl citrate (ATBC), dimethyl sebacate, diethylsebacate, triethyl phosphate, tri(2-ethyl-hexyl)phosphate, tri(p-cresyl) phosphate, diisodecyl adipate (DIDA), glyceryl triacetate, glyceryl tributyrate, dioctyl adipate (DICA), isopropyl myrisate, butyl sterate, lauric acid, trioctyl trimelliate, dioctyl glutatrate (DICG), and mixtures thereof. Tributyl citrate, diisodecyl adipate, and acetyl tributyl citrate are preferred plasticizers, which when present are in an amount of up to thirty percent (30%) by weight of the liquid adhesive composition The amount to be used can be determined by one of ordinary skill in the art, using known techniques without undue experimentation.

Anti-Microbial Agent

In certain embodiments of the present invention, the cyanoacrylate adhesive compositions in the applicator 190 may optionally comprise an antimicrobial agent in an effective amount. The antimicrobial agent is released from the polymer film of the adhesive formed on human or animal skins to inhibit microbial growth and prevent wound or surgical site infections. Suitable antimicrobial agents include, but are not limited to, antibacterial agents such as chlorhexidine and its salts, typical antibiotics, copolymers of vinylpyrrolidone and vinyl acetate, antiseptics, the iodine-containing polymer such as povidone iodine, biguanidine compounds, phenol compounds such as 5-chloro-2-(2,4-dichlorophenoxy)phenol, acridine compounds, quaternary ammonium compounds such as benzalkonium chloride, cetylpridospores, and zephiran, copolymers of vinylpyrrolidone and vinyl acetate cross-linked with polyisocyanates, heavy metal salts such as silver nitrate, and aldehyde compounds such as glutaraldhyde.

Thickening Agent

The cyanoacrylate adhesive in various applicators 190 may optionally contain thickening agents. Suitable thickening agents include, but are not limited to, polycaprolactone, copolymers of alkylacrylate and vinyl acetate, polyalkyl methacrylates, polyalkyl acrylates, lactic-glycolic acid copolymers, lactic acid-caprolactone copolymers, polyorthoesters, copolymers of alkyl methacrylates and butadiene, polyoxalates, and triblock copolymers of polyoxypropylene flanked by two hydrophilic chains of polyoxyethylene. Preferred thickening agents include a partial polymer of cyanoacrylate as disclosed in U.S. Pat. Nos. 8,198,344 and 8,293,838. Preferably the thickening agent is miscible in cyanoacrylate monomer compositions at room temperature.

In summary, the present invention provides a serializable applicator 190 capable of producing precise drops required to secure a catheter on to a body.

EXAMPLES

The following examples are included to more clearly demonstrate the overall nature of the invention. These examples are exemplary, not restrictive, of the invention.

Example 1

A mixture of n-butyl cyanoacrylate and 2-octyl cyanoacrylate in a ratio of 2/8 stabilized by a free radical stabilizer and an anionic stabilizer was stored in the container 130 made of acrylonitrile copolymer. The composition in the container 130 was sterilized by gamma irradiation. Then the shelf life stability was evaluated by accelerated aging at 80° C. for 13 days. Based on ASTM F1980, 13 days of accelerated aging study at 80° C. correlates to 2 years of shelf life at ambient temperatures. At day 13 of the accelerated aging study at 80° C., the viscosity was slightly increased to 24.97 cps from 5.40 at day 0 of the testing, which is well within the specification of 200 cps indicating the composition in the packaging is compatible with the sterilization methods and is able to provide at least 24 months of shelf life.

Example 2

2-Octyl cyanoacrylate composition including a preferred polymerization accelerator of less than 500 ppm, a free radical stabilizer, and an anionic stabilizer was stored in the container 130 made of cyclic olefin copolymer. The shelf life stability of the composition in the container 130 post gamma sterilization was evaluated by the accelerated aging study at 80° C. for 13 days. At day 13 of the accelerated aging study at 80° C., the viscosity was increased to 71.13 cps from 8.52 cps at day 0 of the testing, which is well within the specification of 200 cps indicating the composition in the container 130 is compatible with the sterilization methods and is able to provide at least 24 months of shelf life.

Example 3

A mixture of n-butyl cyanoacrylate and 2-octyl cyanoacrylate, stabilized by a free radical stabilizer and an anionic stabilizer, was stored in the container 130 made of cyclic olefin copolymer. The shelf life stability of the composition in the container 130 post gamma sterilization was evaluated by the accelerated aging study at 80° C. for 13 days. At day 13 of the accelerated aging study at 80° C., the viscosity was increased to 59.87 cps from 4.68 cps at day 0 of the testing, which is well within the specification of 200 cps indicating the composition in the container 130 is compatible with the sterilization methods and is able to provide at least 24 months of shelf life.

Example 4

Shelf life stability of cyanoacrylate compositions in the container 130 and other packages made of different materials under various irradiation sterilizations was studied. The cyanoacrylate compositions stored in the package system of the current invention provided a shelf life of at least 24 months under irradiation techniques such as gamma irradiation. This was confirmed by an accelerated aging test by storing the sterilized packaging containing a sterilized cyanoacrylate composition at 80° C. for 13 days. The investigated compositions were tested for viscosity at different intervals of the aging process. As shown in Table 1, the viscosity of the cyanoacrylate composition in the container 130 after irradiation sterilization slightly increases as the accelerated aging proceeds but the increased viscosity of the aged samples at day 13 is so slight that it does not affect the performance of the cyanoacrylate composition or dispensing of the compositions from the packaging delivery system. In comparison, however, the same cyanoacrylate adhesive compositions contained in other applicators made of only low density polyethylene (LDPE), high density polyethylene (HDPE), and polypropylene, amber HDPE, glass, and polyethylene terephthalate glycol were not found to be as stable upon irradiation sterilization. The cyanoacrylate compositions packaged in other systems as shown in Table 1 below were cured in a few months after the irradiation sterilization, exhibiting an unacceptable shelf life. The cyanoacrylate compositions packaged in the container 130 provide an extended shelf life of at least two years after irradiation sterilization. These observations demonstrate the uniqueness of the package system disclosed as a suitable container 130 for the cyanoacrylate compositions.

TABLE 1

Shelf life stability of cyanoacrylate compositions in different packages under various irradiation sterilizations

| Formula | Package Body and Material | Irradiation | Shelf stability of Liquid Sealant, post-irradiation sterilization |
|---|---|---|---|
| In Example 1 | PP Applicator | Gamma | All cured at month 1 when stored at 40 degree C. |
| In Example 1 | MDPE applicator | Gamma | All cured at month 1 when stored at 40 degree C. |
| In Example 1 | Polypropylene | E-beam | Cured in about a month |
| In Example 1 | Low density polyethylene | E-beam | Cured in about a month |
| In Example 1 | High density polyethylene | E-beam | Cured in about a month |
| In Example 1 | Applicator of the invention | Gamma | At least 24 months |
| In Example 2 | Clear Flint glass bottles | Gamma | Cured upon sterilization |
| In Example 2 | Amber glass bottles | Gamma | Cured upon sterilization |
| In Example 2 | Natural LDPE bottle | Gamma | Too viscous at day 13 when stored at 80 degrees C. |
| In Example 2 | Amber HPDE | E-beam | Cured in about a month |
| In Example 2 | Polypropylene | E-beam | Cured in about a month |
| In Example 2 | Amber glass | E-beam | Cured in about a month |
| In Example 2 | Low density polyethylene | E-beam | Cured in about a month |
| In Example 2 | High density polyethylene | E-beam | Cured in about a month |
| In Example 2 | Applicator of the invention | Gamma | At least 24 months |
| In Example 3 | Polypropylene | E-beam | Cured in about a month |
| In Example 3 | Low density polyethylene | E-beam | Cured in about a month |
| In Example 3 | High density polyethylene | E-beam | Cured in about a month |
| In Example 3 | PP Applicator | Gamma | All cured within 3.5 months |
| In Example 3 | MDPE applicator | Gamma | All cured within 3.5 months |
| In Example 3 | Applicator of the invention | Gamma | At least 24 months |

Example 5

The cyanoacrylate composition in the applicator 190 as well as a conventional catheter dressing product, Opsite, were evaluated to secure Autoguard catheters onto pig skin. The average adhesion strength for securing BD Autoguard catheters using the composition in the applicator 190 and the Opsite product at 30 minutes after application are 2.80 lbf and 0.72 lbf, respectively, indicating that the composition in the applicator 190 of the current invention is about 4 times stronger than that of the Opsite product in terms of securing Autoguard catheters.

Example 6

The cyanoacrylate composition in the applicator 190 as well as a conventional catheter dressing product, the HubGuard® product, were evaluated to secure BD Nexiva catheters onto pig skin. The average adhesion strength for securing BD Nexiva Catheters using a composition in the applicator 190 and the HubGuard® product, at 30 minutes after application are 3.0 lbf and 0.35 lbf, respectively, indicating that the composition in the applicator 190 is about 9 times stronger than that of the HubGuard® product, in terms of securing Nexiva catheters.

Example 7

The cyanoacrylate composition in the applicator 190 as well as a conventional catheter dressing product, the Tegaderm™ 1683 product, were evaluated to secure Autoguard catheters onto pig skin. The average adhesion strength for securing BD Autoguard catheters using the composition in (1) the applicator 190 plus the Tegaderm™ 1683 product and (2) the Tegaderm™ 1683 product alone at 6 hours after application are 5.01 lbf and 1.89 lbf, respectively, indicating that the composition in the applicator 190 plus the Tegaderm™ 1683 product is much stronger than that of the Tegaderm™ 1683 product alone in terms of securing Autoguard catheters.

Example 8

The cyanoacrylate composition in the applicator 190 as well as a conventional catheter dressing product, the Tegaderm™ 9525HP product, were evaluated to secure BD Nexiva catheters onto pig skin. The average adhesion strength for securing BD Nexiva catheters using the composition in (1) the applicator 190 plus the Tegaderm™ 9525HP product and (2) the Tegaderm™ 9525HP product alone at 6 hours after application are 4.07 lbf and 1.68 lbf, respectively, indicating that the composition in the applicator 190 plus the Tegaderm™ 9525HP product is much stronger than that of the Tegaderm™ 9525HP product alone in terms of securing Autoguard catheters.

Example 9

The cyanoacrylate composition in the applicator 190 was evaluated to secure BD Autoguard catheters onto pig skin. The average adhesion strength for securing BD Autoguard catheters using the composition in the applicator 190 at 3 days after application is 3.38 lbf.

Example 10

The cyanoacrylate composition in the applicator 190 was evaluated to secure BD Nexiva catheters onto pig skin. The average adhesion strength for securing BD Nexiva catheters using the composition in the applicator 190 at 3 days after application is 3.02 lbf.

Although illustrated and described above with reference to certain specific embodiments and examples, the present invention is nevertheless not intended to be limited to the details shown. Rather, various modifications may be made in the details within the scope and range of equivalents of the claims and without departing from the spirit of the invention. It is expressly intended, for example, that all ranges broadly recited in this document include within their scope all narrower ranges which fall within the broader ranges.

What is claimed is:

1. An applicator for storing and dispensing an adhesive comprising:
    a) a container with walls defining a chamber, the walls formed of a copolymer of cyclic olefin or acrylonitrile copolymer or formed of multiple layers with the innermost layer including a copolymer of cyclic olefin or acrylonitrile, and a frangible seal covering a proximal end of the chamber, the frangible seal having a side in communication with a stabilized cyanoacrylate monomer adhesive stored in the chamber;
    b) a body comprising a first proximal end and a distal end, a flange extending from the first proximal end of the body having at least one hole, a channel in communication with the hole, the channel extending through the body, and having an opening at the distal end of the body and a grip capable of constricting the channel when inward pressure is applied to the grip, wherein the flange is capable of penetrating the frangible seal when the body and the container are compressed together; and
    c) a rigid tip having
        a second proximal end, in communication with the opening of the channel,
        a terminal end defining an opening of the tip opposite the second proximal end, and
        an outer surface between the second proximal end and the terminal end of the tip,
        wherein outer surface of the tip tapers at a consistent rate between the second proximal end and the terminal end;
    wherein the applicator is activated by compressing the body and the container together whereupon the flange penetrates the frangible seal and allows the adhesive to flow into the hole, through the channel, and out of the rigid tapered tip, and wherein at least the container is sterilized by radiation, and the adhesive stored in the container does not cure upon radiation exposure for at least twenty-four months of shelf storage thereafter.

2. The applicator of claim 1, wherein the cyanoacrylate monomer adhesive comprises a monomer of 2-octyl cyanoacrylate, dodecyl cyanoacrylate, 2-ethylhexyl cyanoacrylate, butyl cyanoacrylate, methyl cyanoacrylate, 3-methoxybutyl cyanoacrylate, 2-butoxyethyl cyanoacrylate, 2-isopropoxyethyl cyanoacrylate, or 1-methoxy-2-propyl cyanoacrylate.

3. The applicator of claim 1, wherein the channel further has a flow restrictor.

4. The applicator of claim 1, wherein the channel is tapered.

5. The applicator of claim 1, wherein the opening of the tip has a diameter between 0.005 mm to 3 mm.

6. The applicator of claim 1, wherein the frangible seal comprises aluminum foil laminated with a copolymer of cyclic olefin on a side in communication with the adhesive stored in the container.

7. An applicator for storing and dispensing an adhesive comprising:
   a) an applicator body with a first proximal end and a first distal end, and defining a housing for a removable adhesive container formed by a copolymer of cyclic olefin or acrylonitrile copolymer or multiple layers with the inner-most layer formed by a copolymer of cyclic olefin or acrylonitrile, the container being capable of fitting within the housing, and further including a frangible seal covering an end of the container and having a side in communication with a stabilized cyanoacrylate monomer adhesive stored in the container;
   b) a body including a second proximal end and a second distal end and containing a channel extending through the body with an opening at the second distal end; and
   c) a rigid tip having
      a second proximal end, in communication with the channel opening,
      a terminal end defining an opening of the tip opposite the second proximal end, and
      an outer surface between the second proximal end and the terminal end of the tip,
      wherein outer surface of the tip tapers at a consistent rate between the second proximal end and the terminal end;
   wherein the applicator is activated by compromising the frangible seal whereupon the adhesive may flow into and through the channel and out of the rigid tapered tip, and wherein at least the container is sterilized by radiation, and the adhesive stored in the container does not cure upon radiation exposure for at least twenty-four months of shelf storage thereafter.

8. The applicator of claim 7, wherein the cyanoacrylate monomer adhesive comprises a monomer of 2-octyl cyanoacrylate, dodecyl cyanoacrylate, 2-ethylhexyl cyanoacrylate, butyl cyanoacrylate, methyl cyanoacrylate, 3-methoxybutyl cyanoacrylate, 2-butoxyethyl cyanoacrylate, 2-isopropoxyethyl cyanoacrylate, or 1-methoxy-2-propyl cyanoacrylate.

9. The applicator of claim 7, wherein the frangible seal comprises aluminum foil laminated with a copolymer of cyclic olefin or acrylonitrile on a side in communication with the adhesive stored in the container.

10. The applicator of claim 1, wherein the channel further has a flow restrictor.

11. The applicator of claim 1, wherein the channel is tapered.

12. The applicator of claim 1, wherein the opening of the tip has a diameter between 0.005 mm to 3 mm.

13. An applicator for storing and dispensing an adhesive comprising:
   a) a container including a wall, an opening, and a chamber containing a stabilized cyanoacrylate monomer adhesive;
   b) the wall further being formed by a copolymer of cyclic olefin or acrylonitrile or multiple layers with the inner-most layer formed by a cyclic olefin or acrylonitrile copolymer;
   c) a frangible seal covering the opening;
   d) a body having a first proximal end, a distal end, and a channel extending through the body with a channel opening at the distal end;
   e) the exterior of the body defining a flexible grip capable of constricting the channel when inward pressure is applied to the grip;
   f) at least one projection attached to the interior of the body, wherein the projection penetrates the frangible seal when the body and the container are compressed together, and
   g) a rigid tip having
      a second proximal end, in communication with the channel opening,
      a terminal end defining an opening of the tip opposite the second proximal end, and
      and outer surface between an opening of the tip opposite the second proximal end, and
      an outer surface between the second proximal end and the terminal end of the tip,
      wherein outer surface of the tip tapers at a consistent rate between the second proximal end and the terminal end;
   wherein the applicator is activated by contacting the body and the container together whereupon the projection penetrates the frangible seal and allows the adhesive to flow into and through the channel and out of the rigid tapered tip, and wherein at least the container is sterilized by radiation, and the adhesive stored in the chamber of the container does not cure upon radiation exposure for at least twenty four months of shelf storage thereafter.

14. The applicator of claim 13, wherein the cyanoacrylate monomer adhesive comprises a monomer of 2-octyl cyanoacrylate, dodecyl cyanoacrylate, 2-ethylhexyl cyanoacrylate, butyl cyanoacrylate, methyl cyanoacrylate, 3-methoxybutyl cyanoacrylate, 2-butoxyethyl cyanoacrylate, 2-isopropoxyethyl cyanoacrylate, or 1-methoxy-2-propyl cyanoacrylate.

15. The applicator of claim 13, wherein the frangible seal comprises aluminum foil laminated with a copolymer of cyclic olefin on a side in communication with the chamber.

16. The applicator of claim 13, wherein the channel further has a flow restrictor.

17. The applicator of claim 13, wherein the channel is tapered.

18. The applicator of claim 13, wherein the opening of the tip has a diameter between 0.005 mm to 3 mm.

19. The applicator of claim 13, wherein the adhesive is stabilized by free radical stabilizers or anionic stabilizers.

* * * * *